United States Patent [19]

Reinherz et al.

[11] Patent Number: 4,788,137
[45] Date of Patent: Nov. 29, 1988

[54] DETECTION OF ACTIVATED T-CELLS

[75] Inventors: Ellis L. Reinherz, Lincoln, Mass.; Andres Alcover, Madrid, Spain; Michael J. Weiss, Brookline, Mass.

[73] Assignee: Dana-Farber Cancer Institute, Inc., Boston, Mass.

[21] Appl. No.: 792,433

[22] Filed: Oct. 29, 1985

[51] Int. Cl.$^4$ ............... G01N 33/53; C12Q 1/04
[52] U.S. Cl. ............................ 435/7; 435/4; 435/30; 435/34; 435/808
[58] Field of Search ............ 435/4, 7, 30, 34, 808; 436/519, 63, 79, 163

[56] References Cited

U.S. PATENT DOCUMENTS 4,599,304  7/1986  Lanier ................................. 435/4

OTHER PUBLICATIONS

Mills et al. (Journ. of Biological Chem)., vol. 260, No. 23, pp. 12500-12507 (1985).
Kim et al. (Clinical Chem.), vol. 31, No. 9, pp. 1481-1485 (1985).
O'Flynn et al. (Biochem. J., vol. 219, 661-666, 1984).
Rabinovitch et al. (Journal of Im-unology, vol. 137, 952-961, No. 3, 1986).
Hunig et al. (Nature, vol. 326, No. 19, pp. 298-301, 1987).
A. Weiss, Proc. Natl. Acad. Sci. USA 81, pp. 4169-4173, 1984.
Mills J. Immunology 134(3) pp. 1640-1643 (1985).
Shapiro J. Immunology 135(4) pp. 2256-2261 (1985).
Imboden J. Immunology 134(2) pp. 663-665 (1985).
M. Weiss Proc. Natl. Acad. Sci. USA 81, pp. 6836-6840, 1985.
Meuer et al. (1984) Cell 36: 897-906.

*Primary Examiner*—Robert J. Warden
*Assistant Examiner*—Robert Benson

[57] ABSTRACT

A method of detecting activated T-cells in a population of cells, the method involving determining intracellular calcium ion concentration or intracellular pH in the cells, a calcium ion concentration two-fold or greater above that of resting T-cells, or a pH increase of over 0.2 pH units, indicating activation.

1 Claim, 2 Drawing Sheets

DETECTION OF ACTIVATED T-CELLS

BACKGROUND OF THE INVENTION

This invention relates to the detection of activated human T-lymphocytes ("T-cells").

Mature human T-cells can exist in a non-activated "resting" state, or in an activated state. Human T-cells can be activated by either of two lineage-specific surface components: the antigen/MHC histocompatibility receptor complex (T3-Ti), and the unrelated T11 molecule. The antigen/MHC receptor complex is comprised of two clonally unique polypeptide chains, termed alpha and beta, which form the putative binding site for antigen/MHC and three noncovalently associated 20–25KD monomorphic T3 molecules thought to be involved in signal transduction. The second structure, the 50KD sheep erythrocyte binding protein, appears to be phylogenetically and ontogenetically more conserved. Although the natural ligand of the T11 system has not yet been identified, monoclonal antibodies to two sets of epitopes, $T11_2$ and $T11_3$ (and to a lesser extent, $T11_1$ and $T11_3$), in concert induce T-cell activation.

T-cells are activated in vivo in response to a variety of stimuli, including infectious agents and sources of foreign antigens, e.g., allografts. The capacity of a patient's T-cells to be activated via the T3-Ti and T11 pathways is an important indication of the status of the patient's immune system. In addition, activation of a patient's T-cells in response to contact with cells from a potential donor of a organ such as a kidney or heart, or of cells, e.g., bone marrow cells, is an indication of histoincompatibility which would lead to rejection of the allograft. Similarly, activation of the donor's T-cells cells indicates probable graft-versus-host disease. Because of the risk of these often fatal developments, histocompatibility typing (known as MHC typing) must be carried out prior to organ or tissue transplantation procedures, often delaying the procedure for several days.

SUMMARY OF THE INVENTION

The invention takes advantage of the discovery that, within minutes of activation via either the T3-Ti or the T11 pathway, there is a large increase in intracellular T-cell calcium ion concentration, as well as an increase in intracellular pH caused by an outflux of hydrogen ions. The invention thus features, generally, a method of detecting activated T-cells in a population of cells, by determining intracellular calcium ion concentration or pH in the cells, a calcium ion concentration two-fold or greater above that of resting T-cells, or a pH increase of over 0.2 units, indicating activation.

In a preferred embodiments calcium ion concentration determination is carried out by bringing the cytoplasm of the cells in contact with a reporter substance e.g., a fluorophore such as indo-1, which undergoes a detectable change when complexed with calcium ions, and detecting the detectable change as an indication of activation. Where a fluorophore is used, it is preferably one which, when complexed with calcium ions or exposed to increased pH, emits or excites at a wavelength different from the wavelength at which the fluorophore emits or excites when not complexed with calcium ions or not exposed to increased pH, or has an altered quantum efficiency (i.e., emits at a greater or decreased intensity) when so complexed or exposed.

The method of the invention can be used to evaluate a patient's immune status, as well as to carry out MHC typing. Both procedures can be carried out quickly, accurately, and with a high degree of automation.

Where a patient's immune status is evaluated using the method, the method involves, prior to calcium ion detection, contacting the cells being assayed (generally, peripheral blood cells) with a substance (e.g., an appropriate antibody) which is capable of activating normal T-cells via either the T11 or the T3-Ti activation pathway. The response (activation or non-activation) of the cells to the stimuli provides valuable diagnostic information on the immune status of the patient. Anti-Ti antibodies are described in U.S. Pat. No. 4,550,086, hereby incorporated by reference. Anti-T3 antibodies are commercially available from Ortho Pharmaceuticals.

Where the method of the invention is used for MHC typing, donor or recipient peripheral blood cells, or cells of both donor and recipient, are labeled prior to calcium concentration or pH determination. The cells which are labeled can either be the cells in which activation is to be detected (i.e., the donor's cells when graft-versus-host disease is being tested for, and the recipient's cells when allograft rejection is being tested for), or the cells not expected to be activated; in either case, the labeling serves to identify the source of the activated cells. Labeling can be carried out using any of a variety of cellular dyes, e.g., fluorescent DNA dyes such as the DNA dyes sold by Hoechst. Alternatively, the label can be a reporter group such as a fluorophore coupled to an antibody which binds to T-cells, but does not participate in activation, e.g., anti-T1 or anti-T12 antibodies. Anti-T12 antibodies are described in U.S. Pat. No. 4,443,427, hereby incorporated by reference.

Where donor and/or recipient cells are prelabeled with a fluorophore, and activation is detected using a fluorophore, the method preferably employs a flow cytometer containing two lasers, one of which illuminates the activation detecting fluorophore, and the other of which illuminates the labeling fluorophore; light of a predetermined wavelength emitted by each is measured, providing both a measure of T-cell activation, and an identification of the source of the activated cells.

Other features and advantages of the invention will be apparent from the following description of the preferred embodiments thereof, and from the claims.

DESCRIPTION OF THE PREFERRED EMBODIMENTS

The drawings are first described.

Drawings

MEASUREMENT OF INTRACELLULAR CALCIUM

Lymphocytes were obtained by Ficoll-Hypaque density centrifugation from healthy donors, and T cells were separated as described in Meuer et al. (1983) Science 222, 1239. Contaminating macrophages were rigorously depleted with anti-Mo2 and complement treatment. Indirect immunofluorescence analysis of the residual population demonstrated no detectable macrophages (<0.5% anti-Mo1 or anti-Mo2 reactive cells). Human T-cell clones were derived from a single donor and propagated in culture as described in Meuer et al., id.

One such clone, a suppressor clone designated 9H5, was loaded with quin-2 acetoxymethylester ("quin-2") a fluorescent indicator of calcium ions, essentially as described in Tsien et al. (1982) J. Cell Biol. 94, 925, as follows. Quin-2 (10 mM) (Calbiochem) in dimethyl sulfoxide was added to $10 \times 10^6$ T-cells per ml to a final concentration of 20 µM in RPMI 1640 medium containing 2.5% serum. After a 45-min incubation at 37° C., cells were centrifuged at 200× g for 10 min, resuspended in the same medium but without quin-2, and incubated for an additional 45 min at 37° C. Celss were then centrifuged and resuspended at $2 \times 10^6$ cells per ml and used immediately.

Monoclonal antibodies used to activate the cells (anti-T3, anti-T8, anti-T11$_2$, and anti-T11$_3$) were produced and screened as described in Meuer et al., id, and used in ascites form. An additional monoclonal antibody directed at the 90-kDA Ti receptor structure on one of the isolated clones (AC3) was generated by standard hybridization techniques after immunization of a BALB/cJ mouse with AC3 cells, as described in Kohler and Milstein (1975) Nature 256, 495. Hybridoma supernatants were screened by means of indirect immunofluorescence on an Epics V cell sorter (Coulter). One antibody, termed anti-Ti$_6$, which reacted only with AC3 and none of 20 additional clones from the same donor or resting peripheral T cells (autologous or allogeneic), was cloned by limiting dilution and injected into pristane primed BALB/cJ mice. The resulting ascites fluid was used as a source of antibody and precipitated a disulfide-linked 90-kDA receptor.

Antibodies were purified by protein A-Sepharose, DEAE-Sepharose, or Sepharose G-200 column chromatography and then covalently linked to CNBr-activated Sepharose 4B (Pharmacia). All Sepharose-coupled reagents were tested for functional integrity by immunoprecipitation from $^{125}$I surface labeled cells of the appropriate specificity.

Figure 1:
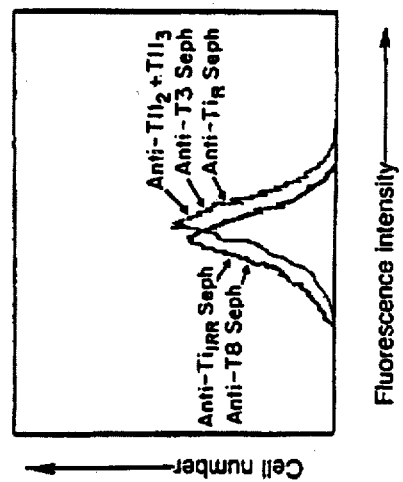

Cells were stimulated with either anti-T3 Sepharose, anti-Ti Sepharose, anti-T8 Sepharose, or a combination of soluble anti-T11$_2$ and anti-T11$_3$ antibodies for 30 min at 37° C., and were then examined using an Epics V dual laser flow cytometer (Coulter). A 5-W argon-ion laser (Spectra-Phycics, Mountain View, Calif., model 164-05) with ultraviolet light output capabilities was used to generate forward light scatter and fluorescence measurements. A suspension of quin-2-loaded cells was injected into a laminar saline stream at a rate of $1.0-1.5 \times 10^3$ cells per sec. A focused beam of ultraviolet laser light (180 mW; multiline, 351.1-363.8 nm) intersected the saline stream as cells flowed through in single file. Unwanted light scatter and fluorescence were eliminated by use of obscuration bars from both scatter and fluorescence detectors. A 408-nm long pass interference filter and a 530-nm short pass interference filter were placed in front of a photomultiplier tube with a detection range between 300 and 720 nm, peaking at 430 nm. Logarithmic and linear integrated signals generated from the stream-laser intersection were collected and organized in the form of 256 channel single-parameter histograms. Scatter-gated viable cells ($1 \times 10^4$) were analyzed, and the resuting histograms provided information regarding percentage reactivity, peak channel location, and relative fluorescence intensity. As shown in FIG. 1, for the representative 9H5 clone, stimulation by anti-T8 Sepharose did not increase cellular fluorescence over background control (anti-Ti$_{IRR}$ Sepharose). In contrast, anti-Ti$_R$ Sepharose, anti-T3 Sepharose, or soluble anti-T11$_2$ and anti-T11$_3$ resulted in an easily detectable shift in mean log fluorescence (channel 95 to channel 110). Moreover, the extent of the fluorescence increase with the latter three stimuli was identical. No further increase in quin-2 fluorescence was observed for any stimulus, even up to 6 hrs. after triggering.

Fluorescence was also recorded using a Hitachi Perkin Elmer MPF-2a spectrofluorimeter (Norwalk, Conn.), excitation at 339 nm (3-nm slit), and emission at 492 nm (11-nm slit), sensitivity of 6. Cells loaded with quin-2 as described above were suspended at $6 \times 10^6$ cells per ml in RPMI 1640 medium without phenol red or vitamins, with 2.5% serum and 10 mM Hepes (pH 7.4). Cells (1.5 ml) were placed in 1-cm quartz cuvettes with a cuvette magnetic stirring bar (Fisher) and were stirred continuously from above. Changes in intracellular calcium activity, which is related to $[Ca^{2+}]_i$, were quantitated by the method of Tsien et al., id. At the end of the experiment, Triton X-100 (1%) was added, followed by an excess of EGTA. The $F_{max}$ was taken to be that obtained after addition of Tritor X-100 (75 arbitrary units) and $F_{min}$ was that obtained after EGTA (34 a.u.). The fluorescence was 46 a.u. before and 65 a.u. after anti-T11$_2$ and anti-T11$_3$ addition. Using a $K_d$ of $115 \times 10^{-9}$M, this corresponds to a change in $[Ca^{2+}]_i$ from ≈50 to $400 \times 10^{-9}$M.

Figure 2:
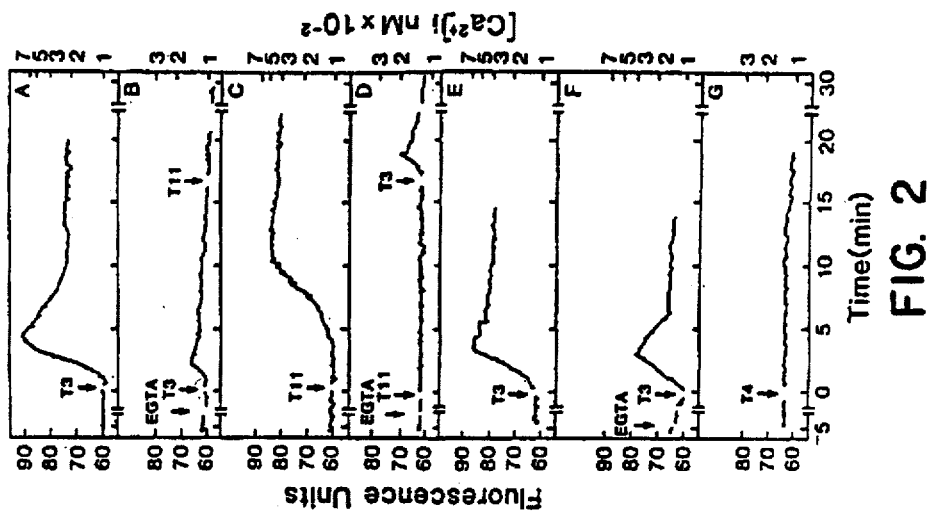
FIGS. 1 and 2 are graphs showing an increase in intracellular Ca ions in activated T-cells, as measured using fluorescence.

FIG. 2 shows a recording of a representative experiment in which quin-2 loaded cells from a helper T-cell clone (AC3) were stimulated with anti-T3 (A,B,E,F) or anti-T11$_2$+anti-T11$_3$ (C,D). In B, D, and F, 3mM EGTA (final concentration) was added to the media 5 min prior to addition of the stimuli. Response of cells activated with anti-T4 antibody is shown in panel G. Fluorescence was determined by spectrofluorimetry as described above with quin-2 loaded cells. The results are representative of 10 assays performed on human T-Cell clones and the tumor T-cell line, REX. As shown, within 2 min of stimulation with anti-T3 or anti-T11$_2$+anti-T11$_3$, quin-2 fluorescence began increasing, reflecting an increase in $[Ca^{2+}]_i$. The fluorescence increased for ≈10 min before reaching a new steady state. This increase in fluorescence reflected an increase in average $[Ca^{2+}]_i$ from ≈50 to $400 \times 10^{-9}$M. In contrast, even a large excess of purified IL-2 (3 units/ml) did not cause any change in quin-2 fluorescence (data not shown). As shown in panels B and D, in the presence of EGTA, the addition of anti-T11$_2$ and anti-T11$_3$ did not result in an increase in quin-2 fluorescence.

The above experiments show that there is a rapid increase in the intracellular Ca$^{2+}$ concentration after triggering of either pathway by specific monoclonal antibodies directed at their various components. Ca$^{2+}$ is thus an important early actor in the physiologic stimulation of human T-cell clones derived from inducer, suppressor, and cytotoxic subclasses. In addition, it was demonstrated that flow cytometry, as opposed to spectrofluorimetric techniques that take an average of the sample, affords a convenient way to examine changes in the fluorescence of discrete populations of cells. This is especially valuable when dealing with polyclonal population of lymphocytes that may exhibit several levels of quin-2 fluorescence and differing responses to a given stimulus.

Simultaneous Measurement of Two Fluorophores

In the following experiments, in addition to quin-2, the fluorescent dyes indo-1, fura-2, diethyloxadicarbocyanine (DiOC$_2$(5)), and phycoerythrin were used. Phycoerythrin was conjugated to anti-T11$_3$ antibody as follows. 1.0 mg of protein A purified anti-T11$_3$ antibody was reacted with 0.5 mg of R-phycoerythrin (pyridyldisulfide derivative) as described in Oi et al. (1982) J. Cell Bio. 93, 981. Anti-T3 (2Ad2) phycoerythrin was obtained from Coulter Immunology (Hialeah, Fla.).

Cells were loaded with 10 μg/ml indo-1 as described above for quin-2 and washed as described for quin-2 using a final concentration for the assay of 10$^6$ cells/ml. After indo-1 loading, cells were incubated for 60 min with 2 nM DiOC$_2$(5). Measurement of indo-1 fluorescence by flow cytometry was performed using an Epics V dual laser flow cytometer (Coulter Electronics, Hialeah, Fla.). A 5W argon ion laser (Spectra-Physics, Mountain View, Calif., model 164-05) with ultraviolet light output capabilities was used to generate forward angle light scatter and fluorescence measurements. A single cell suspension of indo-1 loaded cells was injected into a laminar saline stream at a rate of $1.0-1.5 \times 10^3$ cells/second. A focused laser beam f ultraviolet light (50 mW multi-line 351.1-363.8 mm) intersected the saline stream as cells flowed through in single file order. Unwanted light scatter and fluorescence were eliminated by used of obscuration bars in front of detectors from both scatter and fluorescence. The measurement of indo-1 fluorescence was achieved by using a 408 long pass and a 530 short pass filter combination directly in front of a photomultiplier tube which had a spectral response ranging from 300-700 nm with peak sensitivity at 430 nm.

Data was acquired in either single or two parameter histogram format. For single parameter analysis, logarithmic and linear integrated fluorescence signals generated from single cells intersecting the laser beam were collected and organized in the form of 256 channel histograms. Fluorescence of viable cells, as determined by forward angle light scatter, was analyzed and histograms were generated, providing information as to the percentage reactivity, peak channel location and relative fluorescence intensity. Two parameter 64×64 channel histograms were constructed with time versus log or linear integrated fluorescence along the X and Y axis, respectively. Fluorescence measurements were recorded every 16 sec over a 15 min. period. Baseline fluorescence was established for about 120 sec prior to addition of the stimuli. Measurements were resumed while the sample was gently stirred.

Simultaneous measurements of both indo-1 and DiOC$_2$ (5) fluorescence or indo-1 and phycoerythrin surface labeled antibody fluorescence was achieved by employing a second laser beam, focused approximately 70 u downstream from the UV laser beam. The second beam was a 200 MW, 568.2 nm laser line derived from a krypton ion laser (Spectra-Physics). Forward angle light scatter and indo-1 derived fluorescence signals were delayed in time 7 micro sec until fluorescence signals were generated from the 568.2 m laser line beam. Spectral separation of either indo-1 fluorescence emission and DiOC$_2$(5) dye emission or indo-1 and phycoerythrin fluorescence was accomplished by use of a 590 dichroic filter which reflected longer wavelength light to a photomultiplier tube which had a 595 nm as well as a 610 nm interference filter. Shorter wavelength emission was transmitted through the dichroic filter and the 408 nm long pass/530 nm short pass combination filters were placed in front of the photomultiplier tube responsible for measurement of indo-1 fluorescence. In addition, a 530 short pass filter was placed in front of the scatter sensor to eliminate unwanted light from the 568.2 nm laser line.

Control samples were analyzed to assure minimal spectral emission overlap as well as optimal fluorescence detection. These control samples consisted of cells loaded with no dye, one dye, or combinations.

Figure 3:
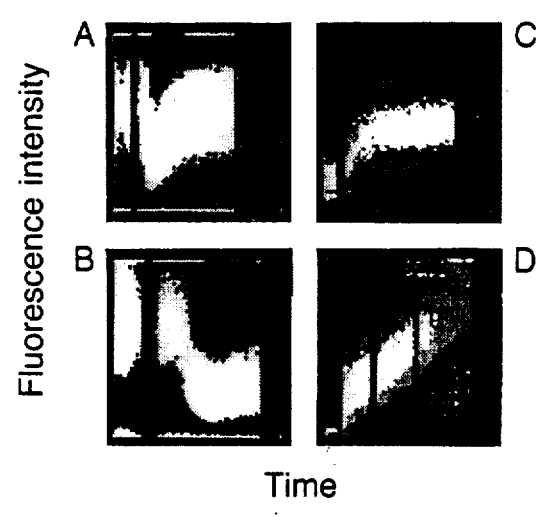
FIG. 3 is a set of panels showing flow cytometric analysis of T-cells activated via T3-Ti or T11.

Referring to FIG. 3, there is shown dual fluorescence flow cytometric analysis of T-cells activated via T3-Ti or T11. Phycoerythrin labeled anti-T3 monoclonal antibody (2Ad2) or unlabeled anti-T11$_2$ plus phycoerythrin labeled anti-T11$_3$ were used to trigger the helper T-cell clone 9H5B. Green (indo-1) and red (phycoerythrin) fluorescence were monitored simultaneously as described above. Panels A and B: indo-1 fluorescence time courses of cells activated via T3 (A) or T11 (B). Panels C and D: Kinetics of binding of T3 (C) and T11$_3$ (D) antibodies labeled with phycoerythrin. Time recordings were over 15 min except for anti-T11$_3$-phycoerythrin, which was performed over 30 min (panel D). Each x-axis division represents 1.25 min (or 2.5 for panel D). In each plot, one dot represents an individual cell; the greater the number of overlapping dots, the lighter the curve. FIG. 3 is representative of 3 assays performed on several different T-cell clones. Estimated time for anti-T3 binding plateau was 2.5 min., and for half saturation of T11$_3$ was 15 min.

Rather than using increase in intracellular Ca$^{++}$ as a measure of activation, increase in intracellular pH can be measured in an analogous fashion. Cells are loaded with a pH-sensitive substance, e.g., a fluorophore whose emission wavelength changes when pH increases. One such fluorophore is 2', 7'-bis (2 carboxyethyl) -5 (and 6) carboxy fluorescein acetoxinethyl ester, available from Molecular Probes, Junction City, Ore. T-cell activation causes a pH increase of 0.2 to 0.5 units (typically 0.4 units), from about 7.0 to 7.4.

OTHER EMBODIMENTS

Other embodiments are within the following claims. For example, reporter substances and labels other than flurophores, and detection methods other than laser-based methods, can be used. Cells can be loaded with chromophores which change color in the presence of calcium ions, for example, and the color change detected spectrophotometrically. Another alternate method would be to employ a dye whose optical density increases or decreases in the presence of calcium ions. Labeling of cells for identification can also be carried out using chromophores, as well as radioisotopes.

We claim:

1. A method of determining whether exposure of a first population of T-cells to a second population of T-cells causes activation of said first population of T-cells, said method comprising
   labeling the cells of said first population of cells with a first fluorophore which is also capable of labelling said second population of cells,
   contacting said first population of cells with said second population of cells to form a mixture of cells, the cytoplasm of said first population of cells being labelled with a second fluorophore which, when complexed with calcium ions or exposed to increased pH, emits or excites at a wavelength different from the wavelength which it emits or excites when not exposed to increased pH or complexed with calcium ions, or having an altered quantum efficiency when so exposed or complexed, placing said mixture of cells in a dual laser flow cytometry system, illuminating said mixture of cells with a first laser capable of causing said first fluorophore to emit light of a predetermined wavelength to cause self-identification of said first population of cells, and illuminating said mixture of cells with a second laser capable of causing said second fluorophore to emit light of a predetermined weavelength as an indication of activation of said first population of cells.

* * * * *